United States Patent [19]

Eisenbraun

[11] Patent Number: 5,735,460
[45] Date of Patent: Apr. 7, 1998

[54] AIR FRESHENER HOUSING COVER

[75] Inventor: Kenneth D. Eisenbraun, Birmingham, Mich.

[73] Assignee: United Industrial Trading Corp., Troy, Mich.

[21] Appl. No.: 660,803

[22] Filed: Jun. 7, 1996

Related U.S. Application Data

[60] Provisional application No. 60/003,243, Sep. 5, 1995.
[51] Int. Cl.⁶ .................................................. A24F 25/00
[52] U.S. Cl. ........................... 239/34; 239/55; 239/57; D23/366
[58] Field of Search .................... 239/34, 53, 55, 239/57, 60, 36; D23/366, 367, 368, 369

[56] References Cited

U.S. PATENT DOCUMENTS

| | | | |
|---|---|---|---|
| 1,723,028 | 10/1929 | Reiner | 239/36 |
| 2,714,649 | 8/1955 | Critzer | 219/19 |
| 2,931,880 | 4/1960 | Yaffe | 219/19 |
| 2,942,090 | 6/1960 | Diehl | 219/19 |
| 3,748,438 | 7/1973 | Costello | 219/271 |
| 3,784,102 | 1/1974 | Stults | 239/36 |
| 4,084,079 | 4/1978 | Costello | 219/271 |
| 4,214,146 | 7/1980 | Schimanski | 219/274 |
| 4,279,373 | 7/1981 | Montrealegre | 239/57 |
| 4,283,011 | 8/1981 | Spector | 239/57 |
| 4,391,781 | 7/1983 | van Lit | 422/125 |
| 4,583,686 | 4/1986 | Martens et al. | 239/34 |
| 4,629,604 | 12/1986 | Spector | 422/124 |
| 4,814,212 | 3/1989 | Spector | 428/14 |
| 4,849,606 | 7/1989 | Martens, III et al. | 219/271 |
| 5,014,913 | 5/1991 | Hoyt et al. | 239/57 |
| 5,136,684 | 8/1992 | Lonker et al. | 392/392 |
| 5,148,983 | 9/1992 | Muniz | 239/34 |
| 5,170,938 | 12/1992 | Dewing | 239/34 |
| 5,201,025 | 4/1993 | Landesberg | 392/392 |
| 5,220,636 | 6/1993 | Chang | 392/392 |
| 5,233,680 | 8/1993 | Fussell | 239/55 |
| 5,240,653 | 8/1993 | Ramkissoon | 261/99 |
| 5,394,506 | 2/1995 | Stein et al. | 392/395 |
| 5,402,517 | 3/1995 | Gillett et al. | 392/386 |
| 5,460,787 | 10/1995 | Colon | 239/55 |
| 5,527,493 | 6/1996 | McElfresh et al. | 239/57 |

*Primary Examiner*—Andres Kashnikow
*Assistant Examiner*—Lisa Ann Douglas
*Attorney, Agent, or Firm*—Gifford, Krass, Groh, Sprinkle, Patmore, Anderson & Citkowski, P.C.

[57] ABSTRACT

An air freshener assembly is disclosed comprising a rigid housing having an interior cavity, an exterior surface having a substantially planar portion and also having a plurality of apertures formed in the substantially planar exterior surface of the rigid housing. An insert containing a volatile fragrant material is disposed within the interior cavity of the rigid housing. A substantially rigid cover member having an upper decorative surface is attached to the substantially planar exterior surface of the rigid housing such that the cover member is supported substantially parallel to and spaced from the housing surface to permit volatilized aromatic gas emitted from the apertures to mix with ambient air.

12 Claims, 2 Drawing Sheets

AIR FRESHENER HOUSING COVER

This application claims the benefit of U.S. Provisional Application No. 60/003,243 filed Sep. 5, 1995.

BACKGROUND OF THE INVENTION

1. Field of the Invention

The present invention relates generally to a device for dispensing fragrance and more particularly to such a device which includes a decorative cover affixed to the exterior of the device so as to be visible to viewers.

2. Prior Art

Air fresheners are used in a variety of locations. Small housings containing air freshening material are affixed to a variety of structures, such as visors or door pockets in automobiles, refrigerator doors, and workbenches. The housings are frequently molded of plastic and contain a volatile fragrant material. The housing has a series of apertures through which the fragrant material may enter and mix with ambient air. The apertures may be adjusted by sliding a plastic partition between the apertures and the air freshening material, permitting the user to regulate the amount of fragrant material being dispensed to the surrounding environment. When the fragrant material has lost its effectiveness, it may be replaced or the housing discarded.

Housings also have an external mechanism by which the housing is affixed to another object. For example, a housing may have a plastic or metal clip extending from the bottom of the housing to permit the housing to be slidably attached to a sun visor or other similar object. Additionally, magnets may be located on the housing to permit attachment to metal objects such as refrigerators or metal shelving. Alternatively, the housings may be permanently attached to an object via an adhesive bond.

SUMMARY OF THE INVENTION

The present invention is directed toward an air freshener assembly having a decorative cover attached to a housing as well as to a cover adapted to be attached to an existing air freshener housing. The housing has an exterior surface having a substantially planar portion. A plurality of apertures are formed in the housing, and an insert containing volatile fragrant material is positioned within the housing such that volatilized aromatic gas may exit the housing through the apertures. The insert is replaceable so that when the fragrant material has evaporated, a new insert may be placed within the housing.

The substantially rigid cover has an upper decorative surface and a lower surface. The lower surface of the cover may be attached to the housing by a variety of means, including adhesive, sonic welding, or through the utilization of common mechanical attachment techniques such as a lock arm and mating hole, or screw. The cover may be removably attached to the housing. The cover is supported above and is substantially parallel to the planar surface of the housing to permit the volatilized aromatic gas which is emitted from the apertures to mix with the ambient air and provide a pleasing aroma. The housing may be attached to a supporting member by a variety of means, such as a clip, magnet, Velcro® or adhesive.

Additionally, a heating element may be utilized to heat the fragrant material, thereby enhancing volatilization of the material. Power may be provided to the heating element from a standard wall socket or vehicle cigarette lighting socket.

The cover is preferably molded of plastic, and the decorative aspect of the upper surface of the cover may be provided by a raised textured surface which is integrally molded into the cover, or a decorative design applied to the cover surface, such as pictures and words including team logos, landscapes, and licensed characters such as Mickey Mouse. The cover may also be manufactured such that a three-dimensional design is molded into the cover which may later be accentuated by the addition of color printing or laminates. The cover may also be manufactured as a picture frame.

Other objects, advantages and applications of the present invention will be made clear by the following detailed description of a preferred embodiment of the invention. The description makes reference to drawings in which:

DETAILED DESCRIPTION OF THE INVENTION

Figure 1:
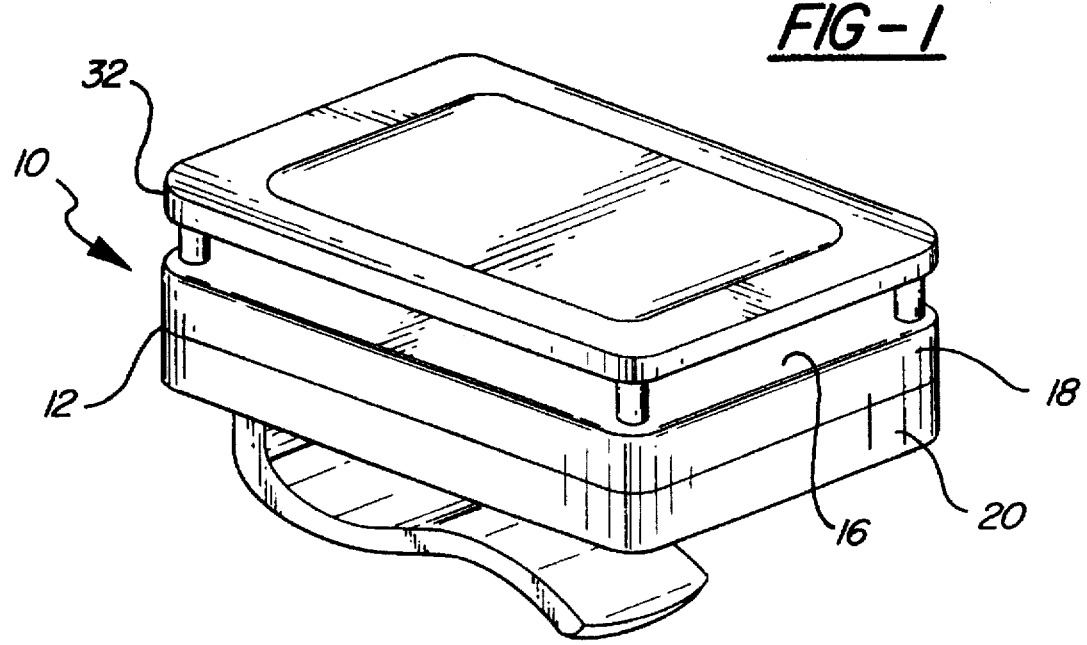
FIG. 1 is a perspective view of a preferred embodiment of the present invention having a picture frame cover and clip for attachment to a supporting member.

The invention, as illustrated in FIG. 1, is an air freshener assembly 10 having a rigid housing 12. In this preferred embodiment, the rigid housing 12 comprises upper half 18 and lower half 20, which may be attached together by a variety of commonly known means, such as an internal rib extending upwardly on lower half 20, the rib mating to a downwardly extending channel on upper half 18. Housing 12 has an exterior surface 16 having a substantially planar portion. The substantially planar portion may be positioned on any exterior surface of housing 12.

Figure 2:
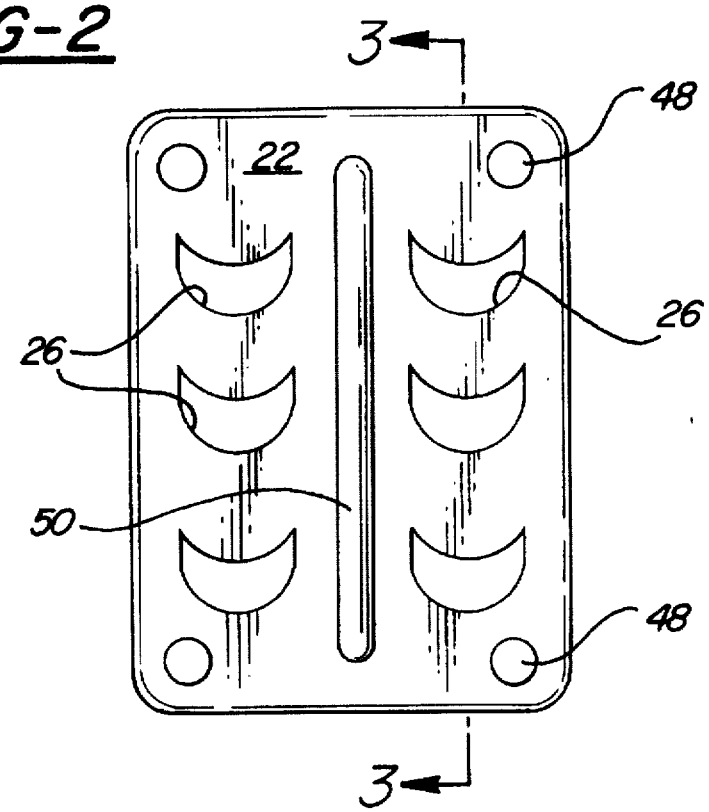
FIG. 2 is a top view of an alternate embodiment of the air freshener housing.
Figure 3:
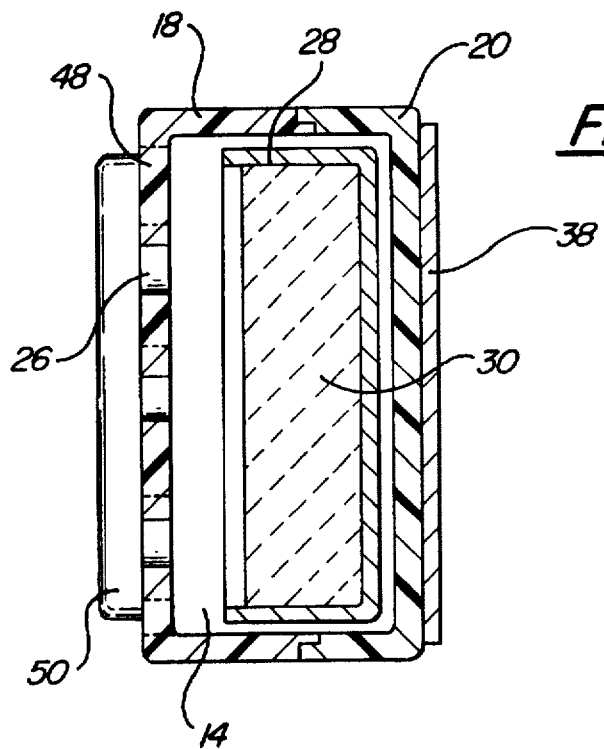
FIG. 3 is a sectional view along line 3—3 of the housing depicted in FIG. 2.

FIGS. 2 and 3 illustrate the housing portion of the air freshener assembly 10. A plurality of apertures 26 are formed in the substantially planar exterior surface 22 of the upper portion 18 of housing 12. The apertures may be shaped as circles, squares or other geometric shapes. A support rib 50 is positioned on the substantially planar portion of the upper half 18 of rigid housing 12. The support rib maintains a predetermined distance between the cover 32 and rigid housing 12. The support ribs 50 may be affixed to either the lower surface of the cover 32 or the housing 12, and may be positioned anywhere along either of these surfaces. Additionally, a plurality of support ribs may be utilized, as illustrated in FIG. 4.

Figure 4:
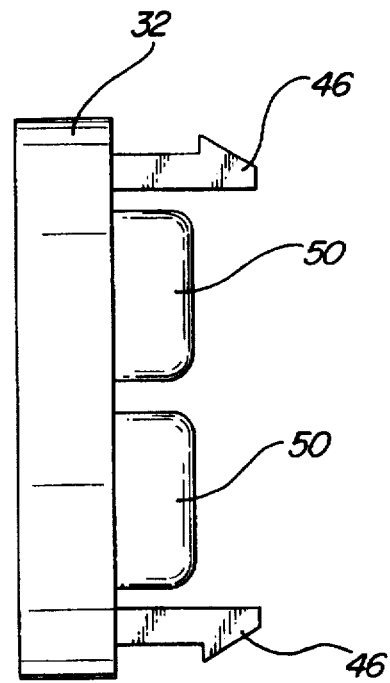
FIG. 4 is a side view of an alternate embodiment of the cover illustrating the flexible lock arms and support ribs.

FIG. 4 depicts an alternate embodiment of the cover 32 wherein flexible lock arms 46 are dimensioned so as to permit mating of the cover with apertures 48, depicted in FIGS. 2 and 3, thereby securing the cover member 32 to the housing 12. Support ribs 50, depicted in FIG. 4, maintain the cover member at a substantially parallel and spaced apart position from the upper surface of the housing 12. Support ribs 50 maintain a minimum distance above the apertures 26 so as to permit volatilized gas emitted from the fragrant material 30 contained in insert 28 positioned within the interior cavity 14 of housing 12 to escape the housing 12 and mix with ambient air, providing a pleasant fragrance in the vicinity of the air freshener assembly. As shown in FIG. 4, magnet 38 may be connected to the housing 12 by adhesive or the like.

Figure 5:
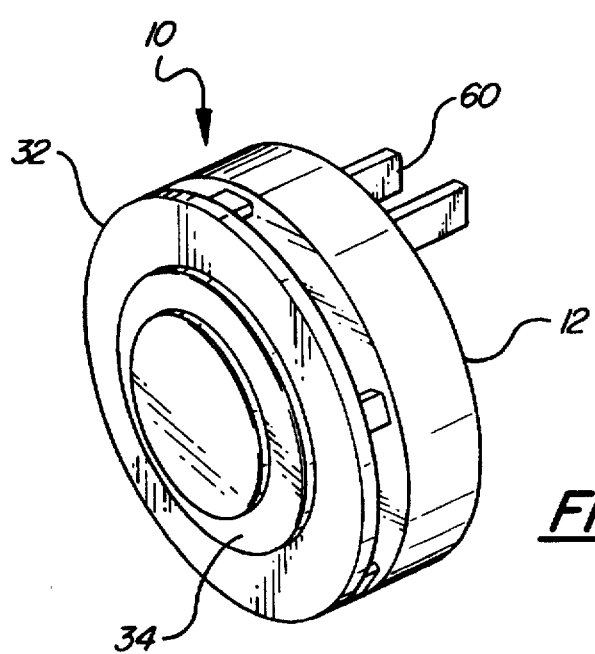
FIG. 5 is a perspective view showing an alternative embodiment of the present invention wherein the air freshener housing with cover is suitable to be plugged into a typical electrical outlet.

The embodiment depicted in FIG. 5 contains a heating element (not shown) integral with the air freshener assembly 10 and is intended to be plugged into a standard wall socket. Prongs 60 are configured to mate with a standard wall socket. Alternatively, prongs 60 may be configured so as to permit insertion of an air freshener housing into a vehicle's cigarette lighter receptacle. The cover member 32 depicted in FIG. 5 illustrates an alternate embodiment of the decorative cover 32 wherein the decorative aspect has been integrally molded into the cover 32.

In alternate embodiments, the cover may be shaped to enhance the decorative aspects of the cover 32. For example, the cover may be shaped as a tree or licensed character. Color printing may be added to the decoratively shaped cover, as well as any of the aforementioned decorative techniques.

Having described the various embodiments of the present invention with reference to the accompanying figures, it will be appreciated that various changes and modifications can be made without departing from the scope or spirit of the invention.

I claim:

1. An air freshener assembly comprising:
   a rigid housing having
   an interior cavity accessible from exteriorly of the housing,
   an exterior surface having a substantially planar portion,
   a plurality of apertures formed in the substantially planar exterior surface of the rigid housing;
   an insert containing a volatile fragrant material, the insert having outer dimensions such that the insert is capable of being disposed within the interior cavity of the rigid housing;
   a substantially rigid cover member having an upper decorative surface and a lower surface, the substantially rigid cover member being substantially planar;
   a plurality of flexible lock arms and an equal number of mating holes for attaching the substantially rigid cover member to the substantially planar exterior surface of the rigid housing, the lock arms and holes aligned so that the lock arms snap into the mating holes, thereby attaching the lower surface of the substantially rigid cover member to the exterior surface of the rigid housing so that the substantially rigid cover member is supported substantially parallel and spaced from the substantially planar exterior surface to permit volatilized aromatic gas emitted from the apertures to mix with ambient air; and
   means for attaching the exterior surface of the rigid housing to a supporting member such that the upper decorative surface of the substantially rigid cover member is visible.

2. The air freshener assembly claimed in claim 1, wherein the means for attaching the exterior surface of the rigid housing member to a supporting member comprises a magnet affixed to the exterior surface of the housing.

3. The air freshener assembly claimed in claim 1, wherein the means for attaching the exterior surface of the rigid housing member to a supporting member comprises a clip extending from the exterior surface of the housing.

4. The air freshener assembly claimed in claim 1, wherein the means for attaching the exterior surface of the rigid housing member to a supporting member comprises adhesive positioned on the exterior surface of the housing.

5. The air freshener assembly claimed in claim 1, wherein the substantially rigid cover further comprises at least one support rib dimensioned so as to maintain a predetermined distance between the substantially rigid cover and the substantially planar exterior surface of the housing.

6. The air freshener assembly claimed in claim 1, wherein the upper decorative surface of the substantially rigid cover comprises a picture frame.

7. In an air freshener assembly having a rigid housing having an interior cavity accessible from exteriorly of the housing, an exterior surface having a substantially planar portion, a plurality of apertures formed in the substantially planar exterior surface of the rigid housing, an insert containing a volatile fragrant material, the insert having outer dimensions such that the insert is capable of being disposed within the interior cavity of the rigid housing, and means for attaching the exterior surface of the rigid housing to a supporting member, the improvement comprising:
   a substantially rigid cover member having an upper decorative surface and a lower surface, the substantially rigid cover member being substantially planar; and
   a plurality of flexible lock arms and an equal number of mating holes for attaching the substantially rigid cover member to the substantially planar exterior surface of the rigid housing, the lock arms aligned with the mating holes so that the lock arms snap into the mating holes thereby attaching the lower surface of the substantially rigid cover member to the exterior surface of the rigid housing, the substantially rigid cover member being supported substantially parallel to and spaced from the substantially planar exterior surface to permit volatilized aromatic gas emitted from the apertures to mix with ambient air.

8. The air freshener assembly claimed in claim 7, wherein the substantially rigid cover further comprises support ribs dimensioned so as to maintain a predetermined distance between the substantially rigid cover and the substantially planar exterior surface of the housing.

9. A cover for use with an air freshener assembly, the air freshener assembly having a rigid housing having an interior cavity accessible from exteriorly of the housing, an exterior surface having at least one portion thereof being substantially planar, a plurality of apertures formed in the substantially planar exterior surface of the rigid housing, an insert containing a volatile fragrant material, the insert having outer dimensions such that the insert is capable of being disposed within the interior cavity of the rigid housing, and means for attaching the exterior surface of the rigid housing to a supporting member, the cover comprising:
   a substantially planar and substantially rigid member having an upper decorative surface and a lower surface; and
   a plurality of flexible lock arms and an equal number of mating holes for attaching the substantially rigid member to the substantially planar exterior surface of the rigid housing, the lock arms aligned with the mating holes so that the lock arms snap into the mating holes thereby attaching the substantially rigid cover member to the exterior surface of the rigid housing, the substantially rigid member being supported substantially parallel to and spaced from the substantially planar exterior surface so as to permit volatilized aromatic gas emitted from the apertures to mix with ambient air.

10. The air freshener assembly claimed in claim 9, wherein the substantially rigid member further comprises support ribs dimensioned so as to maintain a predetermined distance between the substantially rigid member and the substantially planar exterior surface of the housing.

11. An air freshener assembly comprising:

a rigid housing having an interior cavity accessible from exteriorly of the housing, an exterior surface having a substantially planar portion, a plurality of apertures formed in the substantially planar exterior surface of the rigid housing;

a substantially rigid cover member having an upper decorative surface and a lower surface, the substantially rigid cover member being substantially planar;

a plurality of flexible lock arms and an equal number of mating holes for attaching the substantially rigid member to the substantially planar exterior surface of the rigid housing, the lock arms aligned with the mating holes so that the lock arms snap into the mating holes thereby attaching the substantially rigid cover member to the exterior surface of the rigid housing, the substantially rigid member being supported substantially parallel to and spaced from the substantially planar exterior surface to permit volatilized aromatic gas emitted from the apertures to mix with ambient air; and means for attaching the exterior surface of the rigid housing to a supporting member such that the upper decorative surface of the substantially rigid cover member is visible.

12. The air freshener assembly of claim 11, the assembly further comprising an insert containing a volatile fragrant material, the insert having outer dimensions such that the insert is capable of being disposed within the interior cavity of the rigid housing.

* * * * *